(12) United States Patent
Aichinger et al.

(10) Patent No.: US 6,320,070 B1
(45) Date of Patent: Nov. 20, 2001

(54) METHOD FOR PRODUCING (METH) ACRYLIC ACID ESTERS

(75) Inventors: Heinrich Aichinger, Mannheim; Michael Fried, Heidelberg; Gerhard Nestler, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/308,251

(22) PCT Filed: Nov. 21, 1997

(86) PCT No.: PCT/EP97/06513

§ 371 Date: May 25, 1999

§ 102(e) Date: May 25, 1999

(87) PCT Pub. No.: WO98/23576

PCT Pub. Date: Jun. 4, 1998

(30) Foreign Application Priority Data

Nov. 25, 1996 (DE) .............................................. 196 48 746

(51) Int. Cl.$^7$ .................................................. C07C 69/52
(52) U.S. Cl. ............................................ 560/205; 560/218
(58) Field of Search ...................................... 560/205, 218

(56) References Cited

U.S. PATENT DOCUMENTS

| | | | |
|---|---|---|---|
| 3,882,167 | * | 5/1975 | Lohmar et al. ........................ 560/205 |
| 4,250,328 | * | 2/1981 | Fujita et al. ........................... 560/205 |
| 4,280,010 | * | 7/1981 | Erpenbach et al. ................... 560/205 |
| 4,329,492 | * | 5/1982 | Andoh et al. ......................... 560/205 |
| 4,435,594 | * | 3/1984 | Matsumura et al. .................. 560/205 |
| 4,733,004 | * | 3/1988 | Pascoe .................................. 560/205 |
| 5,093,520 | * | 3/1992 | Nestler et al. ........................ 560/218 |
| 5,386,052 | | 1/1995 | Sakakura .............................. 560/205 |
| 5,510,514 | | 4/1996 | Fauconet et al. ..................... 560/218 |

FOREIGN PATENT DOCUMENTS 0 609 127  8/1994 (EP) .
0 618 187  10/1994 (EP) .

OTHER PUBLICATIONS

Chemical Abstracts, vol. 92, AN 163589n, p. 566, 1980, Czech. 179, 808, Jul. 15, 1979.
Kirk–Othmer, Encyclopedia of Chem. Technol., 3$^{rd}$ ed. vol. 1, pp. 347–348, "Acrylic Acid and Derivatives".

* cited by examiner

Primary Examiner—Gary Geist
Assistant Examiner—Taylor V. Oh
(74) Attorney, Agent, or Firm—Oblon, Spivak, McClelland, Maier & Neustadt, P.C.

(57) ABSTRACT

(Meth)acrylic esters are prepared by reacting (meth)acrylic acid with a $C_4$–$C_{12}$-alkanol in the presence of sulfuric acid or a mono-$C_4$–$C_{12}$-alkyl sulfate as catalyst, wherein a) the reaction is carried out in an esterification unit which comprises a first reactor and at least one further reactor, b) a mixture of (meth)acrylic acid, $C_4$–$C_{12}$-alkanol and catalyst which contains not more than 5% by weight of water, based on the sum of the starting materials, is introduced into the first reactor, c) the esterification in the first reactor is conducted without removing ester, alkanol or water to a (meth) acrylic acid conversion of at least 40%, but only so far that the mixture remains a single phase, and d) the esterification is continued in at least one further reactor with the water formed being removed by distillation.

11 Claims, No Drawings

METHOD FOR PRODUCING (METH) ACRYLIC ACID ESTERS

BACKGROUND OF THE INVENTION

1. Field of the Invention

The present invention relates to a process for preparing esters of acrylic acid or methacrylic acid [(meth)acrylic acid].

2. Discussion of the Background (Meth)acrylic esters are generally prepared industrially by esterification of (meth)acrylic acid with alkanols in the presence of strong acids as esterification catalysts (e.g. a mineral acid such as sulfuric acid, phosphoric acid, alkanesulfonic acids or arylsulfonic acids). Such processes are known from, for example, Kirk Othmer, "Encyclopedia of Chemical Technology", Vol. 1, pp. 347–348. The catalyst content of the esterification mixture can vary from tenths of a percent to several percent. When using polybasic mineral acids as catalyst, the mineral acid is easily esterified by the alkanol present to form the monoester which is the actual esterification catalyst. After the esterification is complete, the reaction mixture contains a relatively large amount of this monoester.

The acids used as catalysts and any esters thereof which are formed have to be removed from the reaction mixture before further processing. This is generally achieved by scrubbing and neutralizing the reaction mixture with alkali metal and alkaline earth metal hydroxide solution or carbonate solutions. This results in the formation of wastewater whose disposal is costly and environmentally polluting. If sulfuric acid is used as catalyst, then, as mentioned, the monoester of sulfuric acid with the alkanol concerned is predominantly formed. The salts of the sulfuric acid monoesters, in particular the esters of higher alkanols, are surface-active and on disposal would considerably impair the quality of the wastewater from the process and cause a not inconsiderable loss of useful product. Thus, for economic and ecological reasons, the recovery and reuse of the catalyst is desirable.

The prior art discloses a number of processes which are all, however, encumbered by considerable disadvantages.

EP-A-0 609 127 describes a process for preparing (meth) acrylic esters, with the alcohol component being recovered by acid hydrolysis from the corresponding sulfuric monoester which is formed in the esterification from sulfuric acid and the alcohol. This process is complicated, environmentally polluting and uneconomical.

CZ-B-179 808 describes a process for recovering mineral acids from esterification mixtures by extraction of the esterification mixture with water, concentration of the aqueous phase by distillation and recirculation of the concentrated aqueous catalyst solution thus obtained to the esterification reaction. This process is energy-consuming.

EP-A-0 618 187 (= U.S. Pat. No. 5,386,052) describes a process for preparing (meth)acrylic esters in which the catalyst is extracted with water and the extract is, possibly after concentration by distillation, returned to the esterification reaction. However, this document draws particular attention to the fact that sulfuric acid is unsuitable as catalyst owing to the poor extractability of the monoalkyl sulfate because the large amount of water which would be needed for adequate extraction of the monoalkyl sulfate would adversely affect the esterification reaction. Catalysts used are therefore alkylsulfonic or arylsulfonic acids (column 2, lines 55 ff), but these are considerably more expensive than sulfuric acid.

In all known processes, the esterification of the starting materials and the distillative removal of the water of reaction are carried out in one and the same reaction vessel or in a cascade of similar vessels. Since the distillation capacity of the reactor can only be utilized sufficiently when relatively large amounts of water have been formed by the esterification reaction, the conventional processes are not optimal in terms of the space-time yield and economics.

Increasing the conversion by raising the reaction temperature is possible to only a limited extent because of the polymerization tendency of the acrylic compounds.

SUMMARY OF THE INVENTION

It is an object of the present invention to develop a technically simple and economical process which makes possible high space-time yields under mild conditions and makes do with sulfuric acid as esterification catalyst. In addition, the process should allow the esterification catalyst (sulfuric acid or monoalkyl sulfate) to be separated off very simply and completely from the reaction mixture obtained. Furthermore, the catalyst should be able to be returned directly, i.e. without additional concentration by distillation, to the esterification.

DETAILED DESCRIPTION OF THE PREFERRED EMBODIMENTS

We have found that this object is achieved by a process for preparing (meth)acrylic esters by reacting (meth)acrylic acid with a $C_4$–$C_{12}$-alkanol, preferably a $C_4$–$C_{10}$-alkanol, particularly preferably a $C_4$–$C_8$-alkanol, in the presence of sulfuric acid or a mono-$C_4$–$C_{12}$-alkyl sulfate as catalyst, wherein a) the reaction is carried out in an esterification unit which comprises a first reactor and at least one further reactor, b) a mixture of (meth)acrylic acid, $C_4$–$C_{12}$-alkanol and catalyst which contains not more than 5% by weight of water, based on the sum of the starting materials, is introduced into the first reactor, c) the esterification in the first reactor is conducted without removing ester, alkanol or water to a (meth) acrylic acid conversion of at least 40%, but only so far that the mixture remains a single phase, and d) the esterification is continued in at least one further reactor with the water formed being removed by distillation.

The esterification is carried out in an esterification unit which comprises a first reactor, preferably a simple insulated or uninsulated vessel without stirrer, column or condenser, and a further customary reactor or a plurality of further customary reactors (cascade), preferably with superposed distillation columns, condensers and phase-separation vessels. The contents of these reactors are mixed in a customary manner, e.g. by stirring. The first reactor can also be operated without particular mixing, mixing preferably occurs as a result of injection of the starting materials.

The first reactor is operated at from 60 to 130° C., particularly preferably at from 80 to 110° C., with the water content of the feed mixture (alkanol, (meth)acrylic acid, catalyst) being below 5% by weight, based on the sum of the starting materials, in order to effect a (meth)acrylic acid conversion of at least 40%, in particular at least 50%. However, the conversion must not be continued so far that the resulting water forms a separate phase and the mixture thus becomes a two-phase system. The optimum conversion is generally reached after a residence time of from 30 minutes to 2 hours, in particular about 1 hour.

For the example of the preparation of butyl acrylate, the following table shows the relationship between water content of the feed mixture (acrylic acid, butanol and catalyst) and conversion in the first reactor at 100° C. and a residence time of 1 hour.

| Water content | Conversion |
|---|---|
| 0% | 57% |
| 5% | 50% |
| 10% | 41% |

The esterification is carried out in the presence of sulfuric acid as catalyst and the conditions are selected such that the residual alkanol content in the esterification mixture is at most 5% by weight, in particular at most 3% by weight, based on the esterification mixture.

It has surprisingly been found that the alkanol content has a great influence on the extractability of the monoalkyl sulfate formed from sulfuric acid and alkanol, which ester acts as the actual esterification catalyst (see Table 1). As a result, the catalyst can be extracted with small amounts of water so that the extract can be returned directly to the esterification.

In order to achieve an alkanol content of at most 5% by weight, a high esterification conversion is preferably brought about, e.g. by distilling off the water of reaction, and/or a suitable ratio of the starting materials is selected. When the residual alkanol content is then still more than 5% by weight, the alkanol is distilled off in a conventional distillation apparatus (e.g. column with sieve trays, Raschig rings, or the packing, etc.). Surprisingly, despite the presence of the strongly acid esterification catalyst, no acid-catalyzed secondary reactions such as ether or olefin formation or addition of the alkanol onto the double bond of the (meth) acrylate (Michael addition) are observed to a significant extent.

The distillation is carried out in a customary manner; the distillation conditions depend on the type of alkanol used.

The conditions for the extraction of the catalyst from the esterification mixture are preferably selected such that the catalyst concentration (sulfuric acid and monoalkyl sulfate) in the aqueous phase is at least 20% by weight, in particular at least 30% by weight, based on the aqueous extract, and the degree of extraction is at least 70% by weight, in particular at least 80% by weight, based on the amount of catalyst in the reaction mixture.

In a particularly preferred embodiment, the aqueous, catalyst-containing extract is used for the extraction in order to achieve as high as possible a catalyst concentration in the extract. For this purpose, the extract is preferably circulated with part of the extract being regularly taken off and reintroduced directly into the esterification reaction. The amount taken off is replaced by fresh water.

The esterification mixture is preferably extracted with from about 5 to 20% by weight, in particular from about 5 to 15% by weight, of water, based on the total weight of the esterification mixture.

The aqueous catalyst solution is returned directly without being concentrated to the first reactor.

The extraction can be carried out in a manner known per se. It is preferably carried out in countercurrent, e.g. in columns without energy input, pulsed columns, columns with internal fittings, mixer-settler apparatuses or in static mixers.

The extraction can be carried out at ambient or elevated temperature, but advantageously at from about 15 to 40° C.

The esterification is essentially carried out in a customary manner. The molar ratio of alkanol:acrylic acid or methacrylic acid is generally 1:0.8 –1.2. Examples of $C_4$–$C_{12}$-alkanols are pentanol, hexanol, heptanol, octanol, 2-ethylhexanol, nonanol, 2-propylheptanol, decanol, undecanol, dodecanol and preferably butanols, in particular n-butanol. The sulfuric acid concentration in the reaction mixture is generally from 0.5 to 10% by weight, preferably from 1 to 5% by weight, based on the total mixture.

As polymerization inhibitors, use is made of, for example, phenothiazine, hydroquinone, hydroquinone monomethyl ether or mixtures thereof and possibly air (0.1–10 l/h×1) in an amount of from 100 to 5000 ppm, based on the reaction mixture.

As entrainers, saturated hydrocarbons (e.g. cyclohexane) or aromatics (e.g. toluene) can be used in the process of the present invention; however, the reaction is preferably carried out without additional entrainer.

The reaction temperature in the further reactor is generally from about 70to 160° C., preferably from 90 to 130° C.

The reaction time is generally from about 1 to 10 hours, preferably from 1 to 6 hours.

The reaction can be carried out under atmospheric, subatmospheric or superatmospheric pressure, continuously or batchwise, with the continuous procedure being particularly preferred.

If after the extraction of the catalyst a further extraction/neutralization of the remaining acids (catalyst and (meth)acrylic acid) by means of an aqueous base is necessary, this can be carried out in a conventional extraction apparatus (see above), with the amount of base required being low because of the high degree of extraction of the catalyst and the extraction proceeding, surprisingly, without the phase-separation problems described in EP-A-0 566 074.

The isolation of the ester from the reaction mixture which has been freed of catalyst and possibly remaining carboxylic acid and low boilers is carried out in a customary manner, in particular by distillation, e.g. by distillation in a sieve tray column.

The invention is illustrated by the following example, without being restricted in any way:

688 g/h of acrylic acid, 820 g/h of n-butanol, 22 g/h of sulfuric acid and 1.5 g/h of phenothiazine as polymerization inhibitor are fed continuously to an esterification unit comprising a first reactor (a heatable vessel having a volume of 3.0 l) and three heatable 1 l stirred reactors (cascade) with superposed distillation columns, condensers and separation vessels. The temperature of the prereactor, which is operated without a gas phase, is 110° C., the stirred reactors are at 115° C., 120° C. and 123° C., and the pressure in the reactors is 0.61 bar. A two-phase distillate is obtained at the top of each column. The organic phase is returned as runback to the columns and the aqueous phase is removed.

The reaction product (1353 g/h) comprises, according to analysis, 91.3% of n-butyl acrylate, 3.0% of n-butanol, 0.5% of acrylic acid and 2.45% of mono-n-butyl sulfate. The acrylic acid conversion is 99%, the transformation is 98%.

The reactor product is cooled to 25° C. and extracted with water at 25° C. in a column (3 cm*200 cm, 5 mm Raschig rings), with the ratio of organic phase: aqueous phase being 1:0.15. 100 g/h of aqueous phase are taken from the extraction and replaced by fresh water.

The aqueous phase taken off, which contains 31.2% of mono-n-butyl sulfate (degree of recovery: 90%), is returned directly to the first reactor and the addition of sulfuric acid is reduced to 2.2 g/h. The water content of the total feed to the prereactor is 4.3%. The acrylic acid conversion in the first reactor is 52%, the acrylic acid conversion after the last reactor is unchanged at 99%.

The dependence of the degree of extraction of the catalyst on the n-butanol content of the reaction mixture fed to the extraction was determined by extracting esterification mixtures which had been prepared by esterification of acrylic acid with n-butanol in the presence of sulfuric acid and had different n-butanol contents once with 10% of water at 25° C. in a separating funnel. The results of these experiments are shown in Table 1 and demonstrate the importance of a reaction procedure which keeps the content of unreacted alkanol below 3%.

TABLE 1

| n-butanol content | 0.1% | 2.5% | 5.0% | 10% |
|---|---|---|---|---|
| catalyst content | 1.93% | 1.88% | 1.83% | 1.75% |
| degree of extraction | 89% | 88% | 71% | 55% |
| residual catalyst content | 0.22% | 0.23% | 0.53% | 0.97% |

We claim:

1. A process for preparing (meth)acrylic esters, which comprises:

reacting (meth)acrylic acid with a $C_4$–$C_{12}$-alkanol in the presence of sulfuric acid or a mono-$C_4$–$C_{12}$-alkyl sulfate as a catalyst, wherein
  a) the reaction is carried out in an esterification unit which comprises a first reactor and at least one further reactor,
  b) a mixture of (meth)acrylic acid, $C_4$–$C_{12}$-alkanol and catalyst which contains not more than 5% by weight of water, based on the sum of the starting materials, is introduced into the first reactor,
  c) the esterification in the first reactor is conducted without removing ester, alkanol or water to a (meth) acrylic acid conversion of at least 40%, but only so far that the mixture remains a single phase, and
  d) the esterification is continued in the at least one further reactor with the water formed being removed by distillation until the amount of residual alcohol in the reaction medium is at most 5%.

2. The process of claim 1, wherein the esterification in the first reactor is carried out to a (meth)acrylic acid conversion of at least 50%.

3. The process of claim 1, wherein the esterification in the first reactor is carried out at from 60 to 130° C.

4. The process of claim 1, wherein the esterification in the first reactor is carried out at from 80 to 110° C.

5. The process of claim 1, wherein the esterification in the at least one further reactor is carried out at from 70 to 160° C.

6. The process of claim 1, wherein the esterification mixture obtained in stage d) is extracted with water or a catalyst-containing extract to remove the catalyst.

7. The process of claim 1, wherein the esterification mixture is extracted with from 5 to 20% by weight of water or a catalyst-containing extract, based on the total esterification mixture.

8. The process of claim 1, wherein the degree of extraction is at least 80%.

9. The process of claim 1, wherein the catalyst concentration in the extract is at least 20% by weight, based on the extract.

10. The process of claim 5, wherein the esterification in the at least one further reactor is carried out at from 90 to 130° C.

11. The process of claim 9, wherein the catalyst concentration in the extract is at least 30% by weight.

* * * * *

UNITED STATES PATENT AND TRADEMARK OFFICE
CERTIFICATE OF CORRECTION

PATENT NO.   : 6,320,070 B1
DATED        : November 20, 2001
INVENTOR(S)  : Heinrich Aichinger et al.

It is certified that error appears in the above-identified patent and that said Letters Patent is hereby corrected as shown below:

<u>Column 5,</u>
Line 30, "more than 5%" should read -- more than 3% --.

Signed and Sealed this

Third Day of June, 2003

JAMES E. ROGAN
*Director of the United States Patent and Trademark Office*